United States Patent
Satake et al.

(10) Patent No.: US 8,523,878 B2
(45) Date of Patent: Sep. 3, 2013

(54) METHOD OF PRODUCING MEDICAL INSTRUMENT

(75) Inventors: Kohsuke Satake, Nagoya (JP); Kazuharu Niwa, Nagoya (JP); Ryo Matsushita, Nagoya (JP); Yasuhiko Suzuki, Inazawa (JP); Hiroko Nomura, Ichinomiya (JP); Kazuhiko Nakada, Nisshin (JP)

(73) Assignee: Kowa Company, Ltd., Nagoya-shi (JP)

( * ) Notice: Subject to any disclaimer, the term of this patent is extended or adjusted under 35 U.S.C. 154(b) by 86 days.

(21) Appl. No.: 12/864,074

(22) PCT Filed: Dec. 17, 2008

(86) PCT No.: PCT/JP2008/003817
§ 371 (c)(1),
(2), (4) Date: Jul. 22, 2010

(87) PCT Pub. No.: WO2009/095975
PCT Pub. Date: Aug. 6, 2009

(65) Prior Publication Data
US 2010/0312255 A1    Dec. 9, 2010

(30) Foreign Application Priority Data

Jan. 31, 2008  (JP) ................ 2008-021170

(51) Int. Cl.
*A61F 9/00* (2006.01)
*A61F 2/16* (2006.01)
*A61L 33/00* (2006.01)

(52) U.S. Cl.
USPC ................. 606/107; 623/6.12; 427/2.1

(58) Field of Classification Search
USPC ............ 606/107; 623/6.12; 427/2.1–2.28, 427/230, 2.36, 237, 532, 541, 553, 537, 538; 428/423.1, 423.2, 423.5; 524/500, 503, 507
See application file for complete search history.

(56) References Cited

U.S. PATENT DOCUMENTS 6,238,799 B1 * 5/2001 Opolski .............. 428/423.1
6,491,672 B2 * 12/2002 Slepian et al. ............. 604/267
(Continued)

FOREIGN PATENT DOCUMENTS

JP    A-10-512172    11/1998
JP    A-2000-507997   6/2000
(Continued)

OTHER PUBLICATIONS

International Preliminary Report on Patentability issued Aug. 3, 2010 in International Patent Application No. PCT/JP2008/003817 (with translation).

(Continued)

*Primary Examiner* — Tuan V Nguyen
(74) *Attorney, Agent, or Firm* — Oliff & Berridge, PLC

(57) ABSTRACT

A method of producing a medical instrument whereby a highly hydrophilic and lubricant coating layer having a high durability can be formed by a simple technique and thus highly hydrophilic and lubricant properties can be imparted to a surface of a medical instrument. An intraocular lens insertion instrument having been subjected to a surface treatment as described above is also provided. The method includes preparing a coating solution by mixing at least a water-insoluble polymer having carboxyl group and a polyfunctional reactive compound with an organic solvent; applying this solution on the surface of the medical instrument; conducting crosslinking; and performing a chemical reaction process. The coating layer is made hydrophilic. The intraocular lens insertion instrument is made hydrophilic by forming the coating layer as described above on an inner surface of an insertion tube portion, crosslinking and then performing the chemical reaction process.

9 Claims, 2 Drawing Sheets

(56) References Cited

U.S. PATENT DOCUMENTS

| | | | |
|---|---|---|---|
| 7,687,097 B2 * | 3/2010 | Makker et al. | 427/2.1 |
| 2002/0068180 A1 | 6/2002 | Yang et al. | |
| 2003/0219562 A1 * | 11/2003 | Rypacek et al. | 428/36.91 |
| 2004/0260318 A1 * | 12/2004 | Hunter et al. | 606/153 |
| 2005/0221041 A1 | 10/2005 | Makker et al. | |
| 2006/0229635 A1 | 10/2006 | Hu et al. | |
| 2006/0276894 A1 | 12/2006 | Finley | |

FOREIGN PATENT DOCUMENTS

| | | |
|---|---|---|
| JP | A-2005-537097 | 12/2005 |
| JP | A-2006-500987 | 1/2006 |
| JP | A-2006-510756 | 3/2006 |
| WO | WO 96/22062 | 7/1996 |
| WO | WO 97/29160 | 8/1997 |
| WO | WO 2004/020012 A1 | 3/2004 |
| WO | WO 2004/028406 A1 | 4/2004 |
| WO | WO 2004/056909 A1 | 7/2004 |
| WO | WO 2006/110696 A1 | 10/2006 |
| WO | WO 2006/116601 A2 | 11/2006 |
| WO | WO 2006/130776 A2 | 12/2006 |

OTHER PUBLICATIONS

Search Report dated Feb. 17, 2009 issued in International Patent Application No. PCT/JP2008/003817 (with translation).
Jan. 4, 2013 European Search Report issued in EP 08 87 1959.
Sep. 28, 2012 Chinese Office Action issued in Chinese Patent Application No. 200880125946.3 (with translation).
Mar. 28, 2013 Japanese Office Action issued in Application No. 2009-551330 (w/ English Translation).

* cited by examiner

METHOD OF PRODUCING MEDICAL INSTRUMENT

TECHNICAL FIELD

The present invention relates to a method of producing a medical instrument that is provided with a coating layer on the surface. The invention additionally relates to an intraocular lens insertion instrument furnished with a coating layer.

BACKGROUND ART

When contact lenses and intraocular lenses, insertion instruments for intraocular lenses, endoscopes, catheters, tubes, and various similar classes of medical instruments are used, the surface of the medical instrument frequently comes into direct contact with biological tissue, with the two sliding against one another. However, because most medical instruments are made of materials such as metal or resin, during contact with biological tissue, lubricity is low and hydrophilicity is lacking, thereby posing a risk of problems such as friction-induced deterioration of the medical instrument, or inflammation.

For this reason, techniques have been contemplated in the past to improve lubricity and hydrophilicity of medical instrument surfaces by subjecting the surface of a medical instrument such as a catheter or intraocular lens insertion instrument to a coating process with any of various classes of hydrophilic polymers, as disclosed in Patent Documents 1 to 4.

However, it is not an easy matter to form a stable coating of a hydrophilic polymer on the surface of a hydrophobic base material such as metal or polypropylene, and inability to achieve satisfactory coating strength, endurance, or lubricity was a recurring problem.

Specifically, according to the coating technique disclosed in Patent Document 1 and Patent Document 2, the coating layer formed on the medical instrument surface is produced from a hydrophilic polymer, and a resultant problem is that if the coating comes into contact with water, the polymer elutes into solution so that the coating effect is lost. Other problems include poor cohesion between the coating layer and the coated surface resulting in inability to produce a uniform coating layer, as well as premature peeling of the coating layer as a whole.

The technique disclosed in Patent Document 3 attempts to improve coating durability by forming a primary layer of a polymer such as polyurethane on the surface of the medical instrument, in this case a stent; and then producing a secondary layer of a polymer with a heparin molecule bonded thereto. However, because the process requires forming two coating layers, a resultant problem was increased labor and cost associated with the coating process.

Meanwhile, an intraocular lens insertion instrument, which is another type of medical instrument, is designed to plunge a compactly folded intraocular lens into the eye through an insertion tube of fine tube shape in order to insert the intraocular lens into the eye through a tiny incision made in ocular tissue such as the cornea. However, even if an ophthalmic viscoelastic material is used as a lubricant, a problem encountered during the plunging operation was that, as a result of improper levels or lack of lubricity between the intraocular lens and the inner surface of the insertion tube made of hydrophobic material, the intraocular lens does not plunge in smoothly.

For this reason it was contemplated to improve lubricity with the intraocular lens by producing a coating layer inside the intraocular lens insertion instrument as disclosed in Patent Document 4. However, because a hydrophilic polymer such as water-soluble cellulose is employed as a component of the coating layer, the problems encountered were like those in the techniques disclosed in Patent Documents 1 and 2, namely, weak bonding and cohesion between the coating layer and the hydrophobic surface of the insertion instrument, resulting in a tendency of the coating layer to delaminate. An additional problem was that when the coating layer comes into contact with water during use, water-soluble coating components rapidly elute into solution so that surface lubricity is not sustained. Also, because the coating liquid is a water-based solution, it tends to clump due to high surface energy, making it difficult to form a uniform thin coating layer. For this reason, the intraocular lens insertion instrument was not provided with sufficient lubricity or hydrophilicity needed for pushing out the lens.

Patent Document 1: JP-T 2006-510756
Patent Document 2: JP-T 2005-537097
Patent Document 3: JP-T 2006-500987
Patent Document 4: JP-T 10-512172

DISCLOSURE OF THE INVENTION

Problem the Invention Attempts to Solve

With the foregoing in view, it is accordingly an object of the present invention, in an aspect thereof relating to a method of producing a medical instrument, to provide a method of producing a medical instrument whereby the surface of a medical instrument may be imparted with exceptional hydrophilicity and lubricity by forming a highly durable coating layer with high hydrophilicity and lubricity through a simple method. In an additional aspect relating to an intraocular lens insertion instrument, the present invention provides an intraocular lens insertion instrument adapted to smoothly insert an intraocular lens by virtue of having a coating layer with exceptional hydrophilicity and lubricity formed on the surface of the insertion section.

Means for Solving the Problem

The present invention in the aspect thereof relating to a method of producing a medical instrument and in the aspect thereof relating to an intraocular lens insertion instrument are disclosed below. The elements employed in the following modes of the invention may be adopted at any possible optional combinations. It is to be understood that the modes and technical features of the invention are not limited to those disclosed herein, but may otherwise be recognized based on the teachings disclosed in the entire detailed description and drawings, or that may be recognized by those skilled in the art based on the inventive concept provided by the present disclosure.

First, the invention relating to a method of producing a medical instrument provides a method of producing a medical instrument adapted to impart hydrophilicity and lubricity to the surface of the medical instrument by forming a coating layer on the medical instrument surface, comprising: a coating solution preparation step in which at least (a) a water-insoluble polymer with a carboxyl group and (b) a polyfunctional reactive compound are dissolved in an organic solvent to obtain a coating solution; an application step in which the coating solution is applied to the surface of the medical instrument to form the coating layer; a crosslinking step in which the coating layer undergoes crosslinking; and a chemical reaction step in which a chemical reaction process is carried out to bring about hydrophilization of the crosslinked coating layer.

In the method of producing a medical instrument according to the present invention, for the coating solution, the water-insoluble polymer with a carboxyl group readily dissolves in the organic solvent, and a uniform coating layer may be advantageously formed on the surface of the medical instrument. The term medical instrument herein is used to include catheters, endoscopes, laryngoscopes, tubes, extracorporeal blood circuit tubes, contact lenses, intraocular lenses, intraocular lens insertion instruments, and the like. The surface of a medical instrument herein refers to a concept that includes the component surfaces of various medical instruments, such as inner surfaces, outside surfaces, and tubular inside peripheral surfaces, of which surfaces lubricity between the medical instrument and biological tissue is required during medical procedures.

Due to the presence of the polyfunctional reactive compound in the coating solution, the water-insoluble polymer molecules crosslink with each other, whereby even if some of the bonds of the long-chain water-insoluble polymer are severed for some reason, the decomposed polymer molecule is prevented from dissociating, so that coating layer strength and endurance are markedly improved.

In the present invention, through a simple procedure of subjecting the coating layer containing the water-insoluble polymer with a carboxyl group to a chemical reaction process to bring about hydrophilization, the coating layer can easily be made hydrophilic. Moreover, through crosslinking together of the water-insoluble polymer by the polyfunctional reactive compound, elution of the hydrophilized polymer from the coating layer can be reduced, even if the coating layer comes into contact with water. Moreover, because only the outside surface of the coating layer becomes hydrophilized while the contact face with the surface of the medical instrument does not become hydrophilized, bonding, cohesion, and strength of the coating layer are not impaired, and the layer resists delamination. As a result, a hydrophilic coating of exceptional durability can be easily accomplished through a simple process.

In the present invention, the water-insoluble polymer with a carboxyl group is preferably selected from the group consisting of hydroxypropyl methylcellulose phthalate, hydroxypropyl methylcellulose succinate acetate, cellulose phthalate acetate, and mixtures thereof.

These substances all have the property of becoming water soluble through pH-dependent dissociation of the carboxyl group in the molecule when pH of the solution rises from acidity to neutrality or alkalinity, and are therefore generally referred to as enteric cellulose. In the present invention, formation of the coating is carried out advantageously by utilizing this property. Specifically, in the coating solution preparation step and the application step, because these substances are water-insoluble, admixture with organic solvents such as acetone and coating onto the surface of a medical instrument can take place under favorable conditions; while through a subsequent chemical reaction process, these substances can be readily hydrophilized, thereby rendering the coating layer hydrophilic through a simple procedure, and endowing the medical instrument surface with exceptional lubricity and hydrophilicity.

In the present invention, the coating solution preferably includes 0.1-10 parts by weight of the water-insoluble polymer with a carboxyl group, 0.01-5 parts by weight of the polyfunctional reactive compound, and 1-100 parts by weight of the organic solvent. Formation of the coating layer can be carried out more advantageously according to this formulation.

In the present invention, the polyfunctional reactive compound is selected from the group consisting of isocyanates, epoxies, acid chlorides, acid anhydrides, triazines, active esters, and mixtures of these.

By employing any of these substances as polyfunctional reactive compounds, better crosslinking between the water-insoluble polymer chains can be brought about, and durability of the coating layer can be improved. Specifically, through crosslinking of the polymer molecules through the agency of the polyfunctional reactive compound, elution of the polymer molecules may be advantageously limited, even after the water-insoluble polymer with a carboxyl group has been rendered hydrophilic through the chemical reaction process.

In the present invention, the coating solution preferably includes a surfactant.

By adding a surfactant to the coating solution, hydrophilicity of the coating layer may be further improved. Addition of a surfactant enables the chemical reaction process to take place under more favorable conditions. A leveling (uniform spreading of the film) effect is also produced during application of the coating solution to the medical instrument. It is possible for the surfactant to be added beforehand to the base material of the medical instrument.

In the present invention, during the aforementioned application step, after applying the coating solution onto the surface of the medical instrument, it is preferable to suction the coating solution or to rotate the medical instrument to subject the coating solution to centrifugal force, in order to spread out the coating solution in a layer over the surface of the medical instrument and to eliminate excess coating solution from the medical instrument surface.

Such a process affords a smoother coating layer of uniform thickness, thereby further improving lubricity of the medical instrument surface.

In the present invention, it is preferable to employ a neutralization process as the chemical reaction process in the chemical reaction step.

By so doing, it is possible to readily hydrophilize the water-insoluble polymer through the exceedingly simple procedure of neutralizing the carboxyl groups of the water-insoluble polymer.

Meanwhile, the invention relating to an intraocular lens insertion instrument provides an intraocular lens insertion instrument including an instrument body of generally tubular shape accommodating an intraocular lens set therein, and adapted to move the intraocular lens axially forward by a plunging member inserted into the instrument body from the axial rear while inducing deformation of the lens to smaller size and plunging the lens into the eye through an insertion tube portion disposed at the axial distal end section of the instrument body; wherein the surface of the interior of the insertion tube portion is imparted with hydrophilicity and lubricity by a coating layer formed thereon; and the coating layer is composed of a crosslinked, chemically processed film produced by a coating solution preparation step in which at least a water-insoluble polymer with a carboxyl group and a polyfunctional reactive compound are dissolved in an organic solvent to obtain a coating solution; an application step in which the coating solution is applied to the surface of the medical instrument to form the coating layer; a crosslinking step in which the coating layer undergoes crosslinking; and a chemical reaction step in which a chemical reaction process is carried out to bring about hydrophilization of the crosslinked coating layer.

According to the present invention relating to an intraocular lens insertion instrument, a coating layer comparable to the coating layer formed according to the invention relating to a method of producing a medical instrument described previously may be formed on the inner surface of the intraocular lens insertion tube portion. Specifically, a coating layer endowed with exceptional hydrophilicity and lubricity and having exceptional durability may be formed in the intraocular lens insertion tube portion, thereby preventing sticking between the intraocular lens and the insertion instrument and improper deformation of the intraocular lens during insertion of the intraocular lens, so that the intraocular lens may be consistently plunged in smooth fashion.

KEYS TO SYMBOLS

Figure 1:
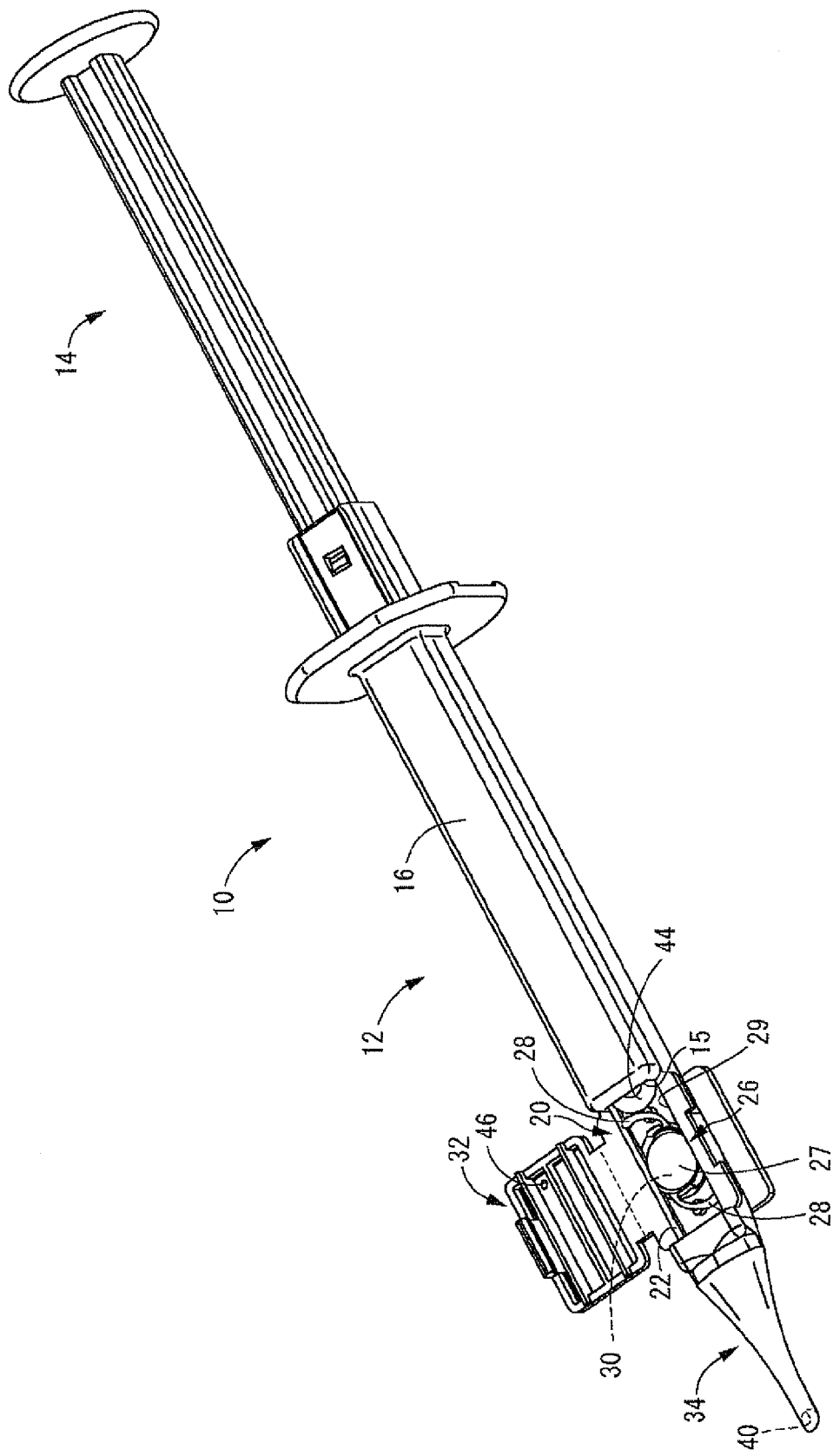
FIG. 1 is a perspective view depicting an intraocular lens insertion instrument according to an embodiment of the invention.

10: insertion instrument; 12: instrument body; 14: plunger; 20: stage; 26: intraocular lens; 34: nozzle portion

BEST MODE FOR CARRYING OUT THE INVENTION

An embodiment of the invention relating to a method of producing a medical instrument is first described hereinbelow in order to provide a more concrete understanding of the present invention relating to a method of producing a medical instrument.

Examples of medical instruments for which the present invention may be implemented in production include various known classes of medical instruments made of metal or resin, such as contact lenses, intraocular lenses, intraocular lens insertion instruments, catheters, stents, and the like. An intraocular lens refers to a lens designed for insertion into the eye to replace the crystalline lens in order to treat a condition such as cataracts. As will be described later, the present invention is particularly well employed in manufacturing intraocular lens insertion instruments.

According to the present invention, a medical instrument having improved hydrophilicity and lubricity can be produced through formation of a coating layer on the surface of these medical instruments. Following is a description of a specific method for forming a coating layer on the surface of a medical instrument.

Firstly, the coating solution in the present invention includes a water-insoluble polymer with a carboxyl group and a polyfunctional reactive compound. As the water-insoluble polymer with a carboxyl group there may be any of various known water-insoluble polymers with carboxyl groups, provided that the objects of the invention are achieved. In preferred practice, at least one of hydroxypropyl methylcellulose phthalate, hydroxypropyl methylcellulose succinate acetate, and cellulose phthalate acetate is employed. Other specific examples are copolymers of (meth)acrylic acid with other radical-polymerizable monomers, for example, acrylic acid-octyl acrylate copolymer or PEMULEN TR-1 (trademark) and EMULEN TR-2 (trademark) made by Nikko Chemicals Co., Ltd., but there is no particular limitation thereto, with the proviso that the compound is a water-insoluble (meth)acrylic acid copolymer. Additional examples are phthalic acid-containing (meth)acrylates such as acryloyloxyethyl phthalic acid monoester, either alone or in a copolymer with another copolymerizable monomer. Another example is polyamic acid, a polymer of tetracarboxylic dianhydride and a diamino compound, which is also a precursor of polyimide. Specific examples are aromatic polyimide synthesized from pyromellitic dianhydride and 4,4'-diaminodiphenyl ether; and aromatic polyimide synthesized from 3,3',4,4'-biphenyltetracarboxylic dianhydride and p-phenylenediamine, and the like. Any one of the various water-insoluble polymers with a carboxyl group may be employed alone, or several different water-insoluble polymers with a carboxyl group may be employed in combination, as the water-insoluble polymer with a carboxyl group in the present invention.

Hydroxypropyl methylcellulose phthalate, hydroxypropyl methylcellulose succinate acetate, or cellulose phthalate acetate employed as the water-insoluble polymer with a carboxyl group in the present invention are all types of cellulose belonging to a group known as enteric cellulose. Enteric cellulose is the name given to cellulose exhibiting special properties whereby when ingested orally, the compound does not dissolve in the stomach, but does dissolve in the intestine. In other words, the compounds have the property of being hydrophobic in low-pH acidic environments such as stomach acid, whereas in environments of high pH, i.e. high alkalinity, such as the intestine, they become hydrophilic through dissociation of the hydrogen atom of the carboxyl group of the molecule.

According to the present invention, by selecting such enteric cellulose in particular for use in the coating solution, in the coating solution preparation step and the application step discussed later, the coating layer can be formed by taking advantage of the property of the compound in untreated form to readily dissolve in solvents; and the coating layer can then be hydrophilized readily by hydrophilization through neutralization in the chemical reaction step.

According to the present invention, the coating solution contains a polyfunctional reactive compound. Specific examples of polyfunctional reactive compounds that may be employed favorably are isocyanates, epoxies, acid chlorides, acid anhydrides, triazines, active esters, and other known substances that are highly reactive by virtue of containing several functional groups. Specific examples of acid chlorides are adipic acid dichloride and the like. Examples of acid anhydrides are maleic anhydride, citraconic anhydride, itaconic anhydride, and other such unsaturated carboxylic acid anhydrides, as well as tetracarboxylic acid dianhydride and VEMA, manufactured by Daicel Chemical. Any one of these various polyfunctional reactive compounds may be employed alone, or a mixture of several different polyfunctional reactive compounds in combination, may be employed as the polyfunctional reactive compound in the present invention.

The coating solution in the present invention preferably includes a surfactant incorporated in addition to the water-insoluble polymer with a carboxyl group and the polyfunctional reactive compound discussed above. Any of various known substances having surfactant action may be employed as the surfactant; however, compounds having functional groups that are able to react with the polyfunctional reactive compound are preferred. Examples include alkyl glyceryl ethers such as glycerol monocetyl ether and glycerol monooleyl ether; glycerol fatty acid esters such as glyceryl monostearate and glyceryl myristate; polyoxyethylene glycerol fatty acid esters such as POE(S) glyceryl monostearate, POE(15) glyceryl monolaurate, and POE(5) glyceryl monooleate; sorbitan fatty acid esters such as sorbitan monolaurate and sorbitan monopalmitate; polyoxyethylene sorbitan fatty acid esters such as POE(20) sorbitan monolaurate (Polysorbate 20), POE(20) sorbitan monopalmitate (Polysorbate 40), and POE(20) sorbitan monostearate (Polysorbate 60); polyoxyethylene hydrogenated castor oil such as POE(10) hydrogenated castor oil and POE(20) hydrogenated castor oil; polyoxyethylene alkyl ethers such as POE(9) lauryl ether, POE(25) lauryl ether, POE(10) cetyl ether, and POE(20) stearyl ether; polyoxyethylene polyoxypropylene alkyl ethers such as POE(10) POP(4) cetyl ether and POE(12) POP(6) decyltetradecyl ether; and polyethylene glycol fatty acid esters such as polyethylene glycol monolaurate (10 EO) and polyethylene glycol monostearate (10 EO). During production of a medical instrument of a resin base material such as polypropylene, it is possible for the surfactant to be added to the base material in advance.

According to the present invention, in the coating solution preparation step, the water-insoluble polymer with a carboxyl group, the polyfunctional reactive compound, and the surfactant are mixed into an organic solvent to prepare the coating solution. Organic solvents that may be employed for the purposes of the present invention include various known organic solvents such as acetone, toluene, xylene, methyl ethyl ketone, ethoxyethyl acetate, tetrahydrofuran, dichloromethane, chloroform, ethyl acetate, and acetonitrile; here, it is especially preferable to select an organic solvent that readily dissolves the water-insoluble polymer with a carboxyl group, has an appropriate level of volatility, and is moreover inert with respect to the polyfunctional reactive compound. For example, where either hydroxypropyl methylcellulose phthalate, hydroxypropyl methylcellulose succinate acetate, or cellulose phthalate acetate is employed as the water-insoluble polymer with a carboxyl group, it is preferable to select acetone.

The specific ingredients and mixture proportions for the coating solution in the present embodiment may be selected freely, within ranges such that the objects of the present invention are attained. In preferred practice, the solution contains a water-insoluble polymer with a carboxyl group at a level of 0.1-10 parts by weight, preferably 0.5-5 parts by weight, and more preferably 1-2 parts by weight; a polyfunctional reactive compound at a level of 0.01-5 parts by weight, preferably 0.05-3 parts by weight, and more preferably 0.1-1 weight part; a surfactant at a level of 0.01-5 parts by weight, preferably 0.05-1 parts by weight; and an organic solvent at a level of 1-100 parts by weight, preferably 2-99 parts by weight, and more preferably 20-31 parts by weight, respectively.

Next, an application step in which the coating solution obtained in the coating solution preparation step discussed above is applied in a layer to the surface of a medical instrument is performed. Prior to the application step, the surface of the medical instrument may undergo a surface treatment step such as plasma treatment, ultraviolet radiation treatment, excimer laser treatment, or the like.

Next, the application step is performed on the surface of the medical instrument to apply a layer of the coating solution onto the surface of the medical instrument. The application step of the present invention may employ known application methods such as dipping, spraying, brush application, or roller application, but it is preferable to employ a method such as the following.

First, an ample amount of freshly prepared coating solution is dripped onto the surface of the medical instrument being coated. Then, with the coating solution resting on the surface, the entire medical instrument is secured to a rotating stage and spun. The resultant centrifugal force acts on the coating solution so as to spread the coating solution towards the outside from the center of rotation; additionally, excess coating solution above the amount needed to cover the surface being coated is eliminated from the medical instrument surface through the action of centrifugal force. By employing this sort of application method, a coating layer with a smooth surface can readily be formed to prescribed thickness with a high degree of accuracy on the surface of the medical instrument. Besides a method utilizing centrifugal force of rotation, a method of suctioning the coating solution to spread out the coating solution while eliminating excess may be employed as the application method. Where the action of centrifugal force is employed, spreading of the coating solution and elimination of the excess may be accomplished in a single spinning operation; or the operation may be carried out in multiple stages at the same or different rotation speeds. Through multi-stage spinning operations the article may be subjected to centrifugal force in respectively different directions. A spinning process and a suction process may be employed in combination as well.

Next, in the crosslinking step according to the present invention a crosslinking process is carried out on the coating solution that was applied to the surface of the medical instrument. The crosslinking process according to the present invention may be selected appropriately from among known processes such as exposure to radiation, UV exposure, heat treatment, or chemical treatment, according to the type and combination of the water-insoluble polymer and polyfunctional reactive compound in the coating layer. A single process such as heat treatment, or a combination of several different processes, may be employed as the crosslinking process of the invention. Where an isocyanate is used as the polyfunctional reactive compound in the invention, it is preferable to use heat treatment for the crosslinking process. The preferred temperature range and treatment time in this case are 40-100° C., and between one minute and 24 hours.

By carrying out such a crosslinking process, the crosslinking reaction is accelerated by the polyfunctional reactive compound to bring about crosslinking of the polymer chains of the water-insoluble polymer with a carboxyl group, bonding them together. The strength and durability of the coating layer are markedly enhanced thereby.

Once the crosslinking step has been completed, the coating layer next undergoes a chemical reaction step in which a chemical reaction process is carried out on the coating layer to impart hydrophilicity. Any of various chemical reaction processes may be employed as the chemical reaction process in the present invention provided that the objects of the invention are attained, but a neutralization process (alkali treatment) is preferred. By subjecting the coating layer to such a neutralization process, the hydrogen atoms of the carboxyl groups of the water-insoluble polymer become dissociated or neutralized, rendering the coating layer hydrophilic as a result. An example of a specific neutralization process method is immersion of the coated medical instrument surface in 0.1-5% sodium bicarbonate aqueous solution for one second to 120 minutes. The neutralizing agent may be selected from compounds such as potassium carbonate, potassium bicarbonate, potassium hydroxide, sodium hydroxide, sodium carbonate, and other salts of alkali metals or alkaline earth metals.

Following the chemical reaction step, a rinsing step and a drying step are carried out by known methods, to complete the coating layer on the medical instrument surface.

In the present embodiment, a hydrophilic coating layer on the medical instrument surface is accomplished through a simple procedure of forming a coating layer of a water-insoluble polymer with a carboxyl group, which is then rendered hydrophilic through a neutralization process. Specifically, it is unnecessary to carry out multilayer coating with a polymer base layer and a hydrophilic polymer layer to produce a hydrophilic coating, because high lubricity and outstanding hydrophilic coating capabilities are afforded by a simple coating structure composed of a single layer only. Thus, a medical instrument having excellent hydrophilicity and lubricity can be obtained without any increase in the number of production steps.

Through crosslinking of the coating solution by the polyfunctional reactive compound, coating components are prevented from eluting into solution if the coating layer comes into contact with a solution. Coating performance can be advantageously maintained thereby.

The present invention relating to a method of producing a medical instrument is preferably implemented in production of an intraocular lens insertion instrument. Specifically, by forming a coating layer on the surface of an intraocular lens insertion instrument in accordance with the present invention, there is readily provided an intraocular lens insertion instrument that exhibits outstanding lubricity between the intraocular lens and the insertion instrument during plunging out of the intraocular lens.

An embodiment of the invention relating to an intraocular lens insertion instrument is described in detail below with reference to the drawings.

First, an intraocular lens insertion instrument 10 according to a first embodiment of the present invention is depicted in FIG. 1. The insertion instrument 10 is composed of an instrument body 12 of generally tubular shape through the interior of which is passed a plunger 14 provided as a plunging member. Herein, 'front' refers to the extending direction of the insertion instrument 10 (left and downward in FIG. 1), and 'up' refers to the upward direction in FIG. 1. 'Left-right direction' refers to the left-right direction of the insertion instrument 10 in rear view (in FIG. 1, the right and downward direction represents left and the left and upward direction represents right). The insertion instrument 10 of the present embodiment has been molded from a base material of polypropylene as the principal component, to which monoglycerol stearate has been added beforehand.

To describe in greater detail, the instrument body 12 has a main tubular section 16 of generally tubular shape. A throughbore 15 of generally oblong cross section passes in the axial direction through the interior of the main tubular section 16.

A stage 20 is formed at the front of the main tubular section 16 of the instrument body 12. As shown in FIG. 1, a recessed slot 22 having a width dimension slightly larger than the diameter dimension of a main body 27 of an intraocular lens 26 extends in the axial direction through the stage 20 and opens upward so that its base face serves as a resting face 30 for the intraocular lens 26.

As shown in FIG. 1, the intraocular lens 26 accommodated in the insertion instrument 10 of the present embodiment includes the main body 27 furnished with an optical region, and a pair of retaining portions 28, 28 that project peripherally outward from the main body 27 and function to position the main body 27 within the eye.

The intraocular lens 26 is arranged on the resting face 30 through an opening 29. At one side of the opening 29 (in the present embodiment, the right side), a cover portion 32 provided as a cover portion is integrally formed with the instrument body 12, and after the intraocular lens 26 has been arranged at the prescribed location, the opening 29 is covered by the cover portion 32.

At the axial distal end section of the instrument body 12 to the front of the stage 20 there is integrally formed a nozzle portion 34 provided as an insertion tube portion. The nozzle portion 34 has gradually tapering contours going from the basal end part of the instrument body 12 side towards the distal end in the projection direction, and a through-bore 36 is formed extending through the entire length in the projection direction.

Figure 2:
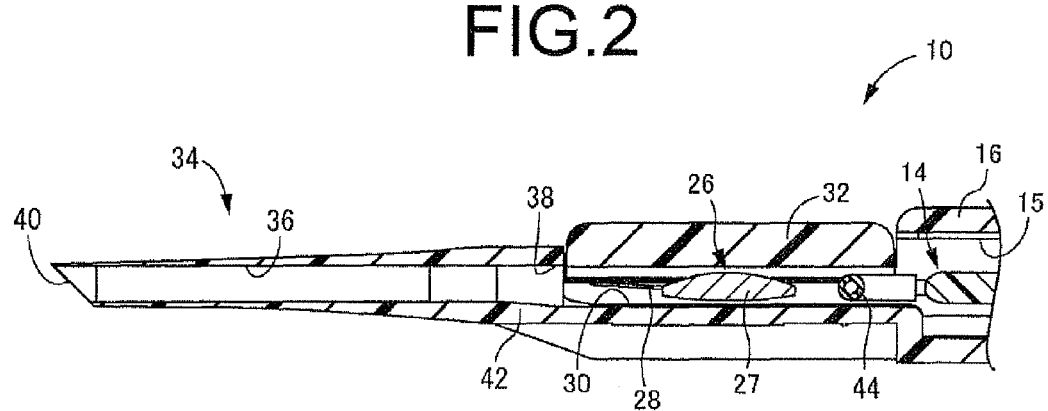
FIG. 2 is a fragmentary enlarged view of the insertion instrument shown in FIG. 1.

As shown in FIG. 2, the through-bore 36 connects with the stage 20 at a basal end opening 38 thereof that opens towards the instrument body 12, and thereby communicates with the stage 20. The through-bore 36 becomes progressively smaller in cross section from the basal end opening 38 towards a distal end opening 40. In the widthwise center part of the base face of the nozzle portion 34 there is formed a projecting guide part 42 of linear shape projecting slightly upward and extending in the axial direction of the instrument body 12.

In this way, the instrument body 12 of the present embodiment is designed as a single member composed of the integrally formed main tubular section 16, stage 20, cover portion 32, and nozzle portion 34. Because the instrument body 12 is a light-transmissive component, even with the stage 20 covered by the cover portion 32, the intraocular lens 26 contained in the instrument body 12 is visible through the cover portion 32.

In the present embodiment, the instrument body 12 is made of polypropylene, but the material of the instrument body 12 may be selected freely from various other materials such as resins or metals. The inner face of the through-bore 36 of the nozzle portion 34 of the instrument body 12 is subjected to the steps previously disclosed in the embodiment of the invention relating to a method of producing a medical instrument, to form a coating layer thereon.

First, the coating solution used to form the coating layer is prepared separately. The specific ingredients and mixture proportions for the coating solution in the present embodiment may be selected freely, within ranges such that the objects of the present invention are attained. In preferred practice, the solution contains a water-insoluble polymer with a carboxyl group at a level of 0.1-10 parts by weight, preferably 0.5-5 parts by weight, and more preferably 1-2 parts by weight; a polyfunctional reactive compound at a level of 0.01-5 parts by weight, preferably 0.05-3 parts by weight, and more preferably 0.1-1 weight part; a surfactant at a level of 0.01-5 parts by weight, preferably 0.05-1 parts by weight; and an organic solvent at a level of 1-100 parts by weight, preferably 2-99 parts by weight, and more preferably 20-31 parts by weight, respectively.

Then, in the coating solution preparation step, hydroxypropyl methylcellulose phthalate, polyisocyanate, and surfactant are mixed and dissolved in acetone by known procedures, to obtain a coating solution.

According to the present embodiment, the application step is carried out in the following manner. First, the desired amount of the coating solution is dripped into the nozzle portion 34 from the opening 29.

Then, using a spin coater (not shown), the instrument body 12 is spun in the horizontal direction about a point situated axially rearward of the nozzle portion 34 so that centrifugal force acts from the stage 20 side towards the distal end opening 40 of the nozzle portion 34. Owing to this centrifugal force, the coating solution is transported from the basal end opening 38 towards the distal end opening 40 and is spread out to cover the entire face of the through-bore 36 through surface tension, while excess coating solution is expelled through the distal end opening 40. As a result, the coating solution becomes applied to generally uniform thickness over the entire face of the through-bore 36 of the nozzle portion 34.

The coating layer is then subjected to a crosslinking step. In the present embodiment, the crosslinking reaction by the polyisocyanate in the coating solution is accelerated through heat treatment at 80° C. for one hour.

Next, as a chemical reaction step for hydrophilizing the coating layer, the entire nozzle portion 34 is immersed for 10 minutes in 1% sodium bicarbonate aqueous solution to neutralize the coating layer. The carboxyl groups of the hydroxypropyl methylcellulose phthalate in the coating layer are thereby neutralized, rendering the coating layer hydrophilic.

Once neutralization is complete, the instrument body 12 inclusive of the nozzle portion 34 undergoes a rinsing process and a drying process to complete the formation of the coating layer on the insertion instrument 10.

The coating layer formation procedure described here is merely exemplary, and any of the modes described previously as embodiments of the invention relating to a method of producing a medical instrument are suitable for implementation for the purpose of forming the coating layer on the insertion instrument 10. In the present embodiment, the coating layer is formed only on the surface of the through-bore 36 of the nozzle portion 34; however, the coating layer could instead be formed over the entire surface of the insertion instrument 10, or on only some other portion thereof.

Once coating of the through-bore 36 is complete, the plunger 14 provided as the plunging member is inserted from the rear into the instrument body 12 and is slipped through the through-bore 15. A tube 44 of generally looped form in top view is attached to the distal end part of the plunger 14. The tube 44 is designed to readily deform in its lengthwise medial section that is positioned at the distal end of the plunger 14.

In the insertion instrument 10 having the above construction, first, with the distal end section of the plunger 14 in its initial position having been inserted from the rear of the instrument body 12 (the position shown in FIG. 1 described previously), the intraocular lens 26 is placed on the resting face 30. The opening 29 of the stage 20 is then covered by the cover portion 32 so that the intraocular lens 26 is positioned accommodated inside the instrument body 12.

The insertion instrument 10 according to this embodiment, with the intraocular lens 26 accommodated therein, is then subjected to a sterilization process etc., then packaged and shipped.

In order to insert the intraocular lens 26 into the eye using the insertion instrument 10 according to the present embodiment, first, with the distal end section of the of the nozzle portion 34 inserted through a surgical incision made in the ocular tissue, the plunger 14 is pushed inwardly. The tube 44 of the plunger 14 thereby comes into contact against the retaining portion 28 of the intraocular lens 26 resting on the resting face 30, and guides the intraocular lens 26 towards the basal end opening 38.

In preferred practice, prior to pushing out the intraocular lens 26, an appropriate lubricant is injected into the interior of the stage 20 or nozzle portion 34. In the present embodiment in particular, an injection hole 46 is formed passing in the thickness direction through the cover portion 32 to allow injection to take place through the injection hole 46 with the cover portion 32 closed. In preferred practice, sodium hyaluronate is used as the lubricant.

The intraocular lens 26 which has been guided into the nozzle portion 34 from the basal end opening 38 is positioned with the projecting guide part 42 abutting the widthwise center section of the main body 27, thereby inducing bowing deformation so that the main body 27 becomes upwardly convex. The intraocular lens 26 inside the through-bore 36 is thereby imparted with initial deformation conforming to the shape of the through-bore 36, and is pushed towards the distal end opening 40.

Pushing the plunger 14 further inward causes the intraocular lens 26 to deform to progressively smaller shape, and then to be pushed out from the insertion instrument 10 through the distal end opening 40 and inserted into the eye.

According to the insertion instrument 10 of the present embodiment, because of the coating layer formed on the surface of the through-bore 36 in the nozzle portion 34, the through-bore 36 interior is imparted with enhanced lubricity, thus preventing improper deformation and sticking between the nozzle portion 34 surface and the intraocular lens 26. This eliminates the problem of the intraocular lens 26 becoming immovably stuck inside the through-bore 36 during pushing of the plunger 14, or of the intraocular lens 26 losing its deformed state, so that insertion of the intraocular lens 26 consistently takes place smoothly.

In the present embodiment, formation of a hydrophilic coating layer on the insertion instrument 10 surface is accomplished through a simple procedure of forming a coating layer of a water-insoluble polymer with a carboxyl group and subjecting the coating to a neutralization process to render it hydrophilic. Specifically, it is unnecessary to carry out two-layer coating with a polymer base layer and a hydrophilic polymer layer to produce the hydrophilic coating, because high lubricity and outstanding hydrophilic coating capabilities are afforded by a simple coating structure composed of a single layer only. Thus, an intraocular lens insertion instrument 10 having excellent lubricity can be obtained without any increase in the number of production steps.

Through crosslinking of the coating solution by a polyfunctional reactive compound, specifically a polyisocyanate, coating components are prevented from eluting into solution even if the coating layer comes into contact with a solution such as a lubricant. Coating performance can be advantageously maintained during service thereby.

While preferred embodiments of the invention relating to a method of producing a medical instrument and of the invention relating to an intraocular lens insertion instrument, have been described in detail, these are merely exemplary, and the invention should in no way be construed as limited by the specific disclosures in these embodiments.

For example, according to the preceding embodiments, the chemical reaction process of the coating layer involved a neutralization process with sodium bicarbonate aqueous solution or the like; however, as an alternative to a neutralization process, a layer of sodium hyaluronate could be applied to the surface of the coating layer to impart further hydrophilicity. Alternatively, sodium hyaluronate may be added to the neutralization solution in the neutralization process described previously, to impart even better lubricity.

Various modifications, alterations, and improvements to the present invention not set forth individually herein may be recognized by those skilled in the art, and are intended to fall within the scope of the invention insofar as there is no departure from the spirit of the invention.

EXAMPLES

A more specific understanding of the present invention is provided by the following description of several examples of the invention, but the invention is in no way limited to the disclosure in the examples. It is to be understood that various modifications, alterations, and improvements to the present invention beyond those taught in the following examples as well as in the specific description herein may be recognized by those skilled in the art insofar as there is no departure from the spirit of the invention.

First, intraocular lens insertion instruments 10 of polypropylene constructed as shown in FIG. 1 were prepared. Coating materials of the compositions indicated in Table 1 below were also prepared.

In the tests, in addition to Examples 1 to 6, as Comparative Examples 1 and 2, a sample was prepared using coating materials containing the same ingredients as Example 1 but not subjected to the chemical reaction process; and a sample was prepared with no coating layer whatsoever, by subjecting the insertion instrument 10 to alkali treatment only. These

TABLE 1

|  |  |  | Ex. 1 | Ex. 2 | Ex. 3 | Ex. 4 | Ex. 5 | Ex. 6 | Comp. Ex. 1 | Comp. Ex. 2 |
|---|---|---|---|---|---|---|---|---|---|---|
| Component | Water-insoluble polymer with a carboxyl group | Hydroxypropyl methylcellulose phthalate | 1 | 1 | 1.25 | — | — | — | 1 | — |
|  |  | Cellulose phthalate acetate | — | — | — | 1.5 | 2 | 2 | — | — |
|  | Polyfunctional reactive compound | AQUANATE 200 | 0.2 | — | — | — | — | — | 0.2 | — |
|  |  | CORONATE HXR | — | 0.2 | 0.1 | 0.1 | 1 | 1 | — | — |
|  | Organic solvent | Acetone | 20 | 20 | 26 | 31 | 20 | 20 | 20 | — |
|  | Surfactant | TL-10 | — | — | — | — | — | 1 | — | — |
|  |  | Monoglyceride stearate | — | — | 0.05 | 0.1 | — | — | — | — |
| Chemical reaction process |  |  | Alkali | Alkali | Alkali | Alkali | Alkali | Alkali | None | Alkali |
| Evaluation result |  |  | ◉ | ○ | ◉ | ◉ | Δ | ◉ | X | X |

Unit: parts by weight

Specifically, in Examples 1 to 6, 1-1.25 parts by weight of hydroxypropyl methylcellulose phthalate or 1.5-2 parts by weight of cellulose phthalate acetate were included as the water-insoluble polymer with a carboxyl group. In each example, 0.2-1 weight part of a polyisocyanate was included as the polyfunctional reactive compound. More specifically, either AQUANATE 100, a water dispersing type of polyisocyanate manufactured by Nippon Polyurethane Industry Co., Ltd., or CORONATE HXR, a hexamethylene diisocyanate multimer manufactured by Nippon Polyurethane Industry Co., Ltd., was used. The organic solvent was acetone included in an amount of 20-31 parts by weight. In Examples 3, 4, and 6, the surfactant was TL-10, which is a polyoxyethylene(20) sorbitan monolaurate manufactured by Nikko Chemicals Co., Ltd. or monoglyceride stearate, respectively included in amounts of 0.05-1 parts by weight.

After the coating materials having the above compositions were combined to prepare coating solutions, using a pipetting system, 100 μL aliquots were dispensed into the nozzle portion 34 of the insertion instruments 10. The dispensed aliquots were then quickly spun at 1500 rpm for 5 seconds using a spin coater in order to spread out the solution over the entire surface of the nozzle portion 34 and to eliminate excess coating solution through the distal end opening 40. Subsequently, after bringing about crosslinking through heat treatment at 80° C. for one hour, the nozzle portion 34 was immersed for 10 minutes in 1% sodium bicarbonate aqueous solution to effect a neutralization process. The insertion instruments 10 were then rinsed and dried.

The coated intraocular lens insertion instruments 10 prepared in the above manner were then subjected to tests of plunging an intraocular lens 26. Specifically, first, VISCOKING 0.85 (TM), a sodium hyaluronate preparation made by Showa Yakuhin Kako Co., Ltd., was applied in a suitable quantity to the nozzle portion 34 as an ophthalmic surgical viscoelastic substance; and an acrylic foldable intraocular lens 26 was arranged thereon, and then plunged out with the plunger 14.

were evaluated for lubricity during plunging in the same manner as for Examples 1 to 6.

The results of evaluation of lubricity during plunging of intraocular lenses 26 in Examples 1 to 6 and in Comparative Examples 1 and 2 are shown in Table 1, using the symbols ◉, ○, Δ, and x. In Table 1, samples affording very good lubricity and smooth plunging are designated by ◉; those having no problem with lubricity but slight detectable resistance during plunging are designated by ○; those having satisfactory lubricity but exhibiting some sticking if the intraocular lens 26 pauses inside the nozzle portion 34 are designated by Δ; and those lacking any lubricity so that sticking prevented the intraocular lens 26 from being plunged out of the nozzle portion 34 are designated by x.

From the results in Table 1, it is apparent that good lubricity was attained in all of the Examples 1 to 6, whereas no lubricity whatsoever was attained in either Comparative Example 1 or 2.

Specifically, it was demonstrated that excellent hydrophilicity and lubricity are attained through a combination of the specific coating material compositions of Examples 1 to 6 and alkali treatment carried out as a chemical reaction process.

The invention claimed is:

1. A method of producing a medical instrument adapted to impart hydrophilicity and lubricity to a surface of the medical instrument by forming a coating layer on the medical instrument surface, comprising:

a coating solution preparation step in which at least a water-insoluble polymer with a carboxyl group which is selected from the group consisting of hydroxypropyl methylcellulose phthalate, hydroxylpropyl methycellulose succinate acetate, cellulose phthalate acetate, and mixtures thereof, and a polyfunctional reactive compound are dissolved in an organic solvent to obtain a coating solution;

an application step in which the coating solution is applied to the surface of the medical instrument to form the coating layer;

a crosslinking step in which the coating layer undergoes crosslinking; and a chemical reaction step in which a chemical reaction process that is an alkali treatment is carried out to bring about hydrophilization of the crosslinked coating layer.

2. The method of producing the medical instrument according to claim 1, wherein the coating solution includes 0.1-10 parts by weight of the water-insoluble polymer with a carboxyl group, 0.01-5 parts by weight of the polyfunctional reactive compound, and 1-100 parts by weight of the organic solvent.

3. The method of producing the medical instrument according to claim 1, wherein the polyfunctional reactive compound is selected from the group consisting of isocyanates, epoxies, acid chlorides, acid anhydrides, triazines, active esters, and mixtures of these.

4. The method of producing the medical instrument according to claim 1, wherein the coating solution includes a surfactant.

5. The method of producing the medical instrument according to claim 1, wherein the application step further comprises the steps of, after applying the coating solution onto the surface of the medical instrument, suctioning the coating solution in order to spread out the coating solution in a layer over the surface of the medical instrument and to eliminate excess coating solution from the medical instrument surface.

6. The method of producing the medical instrument according to claim 1, wherein the application step further comprises the steps of, after applying the coating solution onto the surface of the medical instrument, rotating the medical instrument to subject the coating solution to centrifugal force in order to spread out the coating solution in a layer over the surface of the medical instrument and to eliminate excess coating solution from the medical instrument surface.

7. The method of producing the medical instrument according to claim 1, wherein the chemical reaction process in the chemical reaction step comprises a neutralization process.

8. The method of producing the medical instrument according to claim 1, wherein the medical instrument comprises an intraocular lens insertion instrument.

9. An intraocular lens insertion instrument comprising:

an instrument body of generally tubular shape accommodating an intraocular lens set therein, and including an insertion tube portion disposed at an axial distal end section of the instrument body; and a plunging member inserted into the instrument body from an axial rear and adapted to move the intraocular lens axially forward while inducing deformation of the lens to smaller size and plunging the lens into an eye through the insertion tube portion, wherein:

a surface of an interior of the insertion tube portion is imparted with hydrophilicity and lubricity by a coating layer formed thereon; and the coating layer is composed of a crosslinked, chemically processed film produced by a coating solution preparation step in which at least a water-insoluble polymer with a carboxyl group which is selected from the group consisting of hydroxypropyl methylcellulose phthalate, hydroxylpropyl methycellulose succinate acetate, cellulose phthalate acetate, and mixtures thereof, and a polyfunctional reactive compound are dissolved in an organic solvent to obtain a coating solution; an application step in which the coating solution is applied to the surface of the instrument to form the coating layer; a crosslinking step in which the coating layer undergoes crosslinking; and a chemical reaction step in which a chemical reaction process that is an alkali treatment is carried out to bring about hydrophilization of the crosslinked coating layer.

* * * * *